US 6,689,163 B2

(12) United States Patent
Lytle

(10) Patent No.: US 6,689,163 B2
(45) Date of Patent: *Feb. 10, 2004

(54) ANNULOPLASTY RING HOLDER

(75) Inventor: Thomas W. Lytle, Round Rock, TX (US)

(73) Assignee: Carbomedics Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/109,031

(22) Filed: Mar. 28, 2002

(65) Prior Publication Data
US 2002/0169503 A1 Nov. 14, 2002

Related U.S. Application Data

(63) Continuation of application No. 09/288,400, filed on Apr. 8, 1999, now Pat. No. 6,406,492.

(51) Int. Cl.[7] .................................................. A61F 2/24
(52) U.S. Cl. ..................................................... 623/2.11
(58) Field of Search ...................... 623/2.11, 2.36–2.42, 623/FOR 101

(56) References Cited

U.S. PATENT DOCUMENTS

| 3,409,013 A | 11/1968 | Berry ........................ 128/303 |
| 3,656,185 A | 4/1972 | Carpentier ........................ 3/1 |
| 4,042,979 A | 8/1977 | Angell ........................ 3/1.5 |
| 4,055,861 A | 11/1977 | Carpentier et al. ............. 3/1.5 |
| 4,144,046 A | 3/1979 | Esposito ........................ 71/86 |
| 4,164,046 A | 8/1979 | Cooley ........................ 3/1.5 |
| 4,290,151 A | 9/1981 | Massana ........................ 3/1.5 |
| 4,489,446 A | 12/1984 | Reed ........................... 3/1.5 |
| 4,602,911 A | 7/1986 | Ahmadi et al. ................ 623/2 |
| 4,917,698 A | 4/1990 | Carpentier et al. ............. 623/2 |
| 5,011,481 A | 4/1991 | Myers et al. .................. 606/1 |
| 5,041,130 A | 8/1991 | Cosgrove et al. .............. 623/2 |
| 5,061,277 A | 10/1991 | Carpentier et al. ............. 623/2 |
| 5,201,880 A | 4/1993 | Wright et al. .................. 623/2 |
| 5,258,021 A | 11/1993 | Duran ........................... 623/2 |

(List continued on next page.)

FOREIGN PATENT DOCUMENTS

| WO | WO 96/39942 | 12/1996 |
| WO | WO 99/29269 | 6/1999 |

OTHER PUBLICATIONS

Chacques, J.C., et al., "Absorbable Rings for Pediatric Valvuloplasty",SupplementIV Circulation, vol. 82, No. 5, Nov. 1990, pp. IV–82–IV–88.

Primary Examiner—Corrine McDermott
Assistant Examiner—Alvin Stewart
(74) Attorney, Agent, or Firm—Williams, Morgan & Amerson, P.C.

(57) ABSTRACT

The invention, in a first aspect, is an apparatus for holding a flexible annuloplasty ring during implantation. The apparatus has a top piece including a bottom surface sized to engage substantially all of the inner diameter of the annuloplasty ring and finished to grip the annuloplasty ring; a bottom piece including a top surface sized to engage substantially all of the inner diameter of the annuloplasty ring and finished to grip the annuloplasty ring; and a haft capable of engaging the top and bottom pieces to clamp the annuloplasty ring therebetween. In a second aspect, the invention is a method of manipulating a flexible annuloplasty ring for implantation. The method involves disposing the annuloplasty ring between a top piece and a bottom piece; and engaging the top piece and the bottom piece with a haft to clamp the annuloplasty ring between the top and bottom pieces.

10 Claims, 4 Drawing Sheets

U.S. PATENT DOCUMENTS

| | | | |
|---|---|---|---|
| 5,306,296 A | 4/1994 | Wright et al. | 623/2 |
| 5,350,420 A | 9/1994 | Cosgrove et al. | 623/2 |
| 5,522,884 A | 6/1996 | Wright | 623/2 |
| 5,552,884 A | 9/1996 | Li et al. | 356/243 |
| 5,578,076 A | 11/1996 | Krueger et al. | 623/2 |
| 5,593,424 A | 1/1997 | Northrup, III | 606/232 |
| 5,669,919 A | 9/1997 | Sanders et al. | 606/148 |
| 5,674,279 A | 10/1997 | Wright et al. | 623/2 |
| 5,683,402 A | 11/1997 | Cosgrove et al. | 606/150 |
| 5,776,189 A | 7/1998 | Khalid | 623/2 |
| 5,972,030 A * | 10/1999 | Garrison et al. | 623/2.11 |
| 6,406,492 B1 * | 6/2002 | Lytle | 623/2.11 |

* cited by examiner

ANNULOPLASTY RING HOLDER

The present application is a continuation of U.S. patent application Ser. No. 09/288,400, filed Apr. 8, 1999, now U.S. Pat. No. 6,406,492, which is specifically incorporated by reference herein in its entirety.

BACKGROUND OF THE INVENTION

1. Field of the Invention

The present invention relates to a prosthesis for a natural human heart that may be used for the surgical correction of a deformed heart valve. In particular, the present invention relates to a holder for a flexible annuloplasty ring prosthesis for use in properly positioning the annuloplasty ring about the valve annulus during implantation.

2. Description of the Related Art

The human heart includes four valves, each comprised of several cusps, that control the flow of blood through the heart. The geometry of these valves is important in their function. More particularly, the geometry helps ensure cusps of the valve overlay each other to assist in controlling the regurgitation of the blood during ventricular contraction. Diseases and certain natural defects to heart valves can impair the functioning of the cusps in preventing regurgitation. For example, certain diseases dilate the heart valve annulus. Dilation may also deform the valve geometry or shape, thereby displacing one or more of the valve cusps from the center of the valve. Other diseases or natural heart valve defects result in deformation of the valve annulus with little or no dilation.

Various surgical procedures have been developed to correct deformations of the valve annulus and retain the intact natural heart valve. These surgical techniques involve repairing the shape of the dilated or elongated valve. Such techniques, generally known as "annuloplasty," require surgically restricting the valve annulus to minimize dilation. Typically, a prosthesis known as an "annuloplasty ring" is sutured around the base of the valve leaflets. The annuloplasty ring reshapes the valve annulus and restricts the movement of the valve annulus during the opening and closing of the valve.

Initially, the annuloplasty rings were designed as rigid frame members, to correct the dilation and reshape the valve annulus to the natural state. This type of annuloplasty ring is referred to as "rigid," and they are still in use today. Rigid annuloplasty rings are formed from a metallic or other rigid material that flexes very little, if at all, during the normal valve operation. Rigid annuloplasty rings adequately promote proper valve performance by restricting valve dilation and reshaping the valve annulus. However, their rigidity prevents the normal flexibility of the valve annulus and may contribute to left ventricular outflow tract obstruction. Another disadvantage with a highly rigid annuloplasty ring is the tendency of the sutures to tear during the normal movement of the valve annulus.

Some in the art have therefore suggested using completely flexible annuloplasty rings. Flexible annuloplasty rings typically include an inner support formed from a flexible material. This support is wrapped in a woven, biocompatible cloth material. Resistance to the dilation of the annulus during the opening and closing of the valve is obtained by properly suturing the ring about the valve annulus. One disadvantage with completely flexible annuloplasty rings is that, during the implantation process, the ring may become bunched at localized areas. This bunching results in the phenomenon known as multiple plications of the annuloplasty ring. One consequence of this phenomenon is variability of the ability of the ring to control the shape of the valve annulus. The bunched areas of the ring tend to provide a more rigid area in comparison to the other portions of the ring, which distorts the valve annulus during valve operation.

One approach sutures the annuloplasty ring to a rigid plastic holder that maintains the ring in its proper shape during the procedure. The holder is in turn releasably secured to a bendable handle that can be formed by the surgeon to facilitate positioning of the ring and holder in the heart concentrically and coplanarly with the annulus of the valve to be repaired. Once the holder is placed and sutures initiated, the handle is withdrawn to give the surgeon room to work and properly see the annulus. When the procedure is completed, valve closure is tested by injecting saline solution. The sutures attaching the ring to the holder are then cut, and the handle and holder are removed, leaving the ring in place.

A problem arises in the release and reattachment of the handle. Because the handle is bent, and because rotary stress on the holder and ring is undesirable, rotary movement (and, for that matter, axial movement also) of the handle during release and attachment must be minimized. The prior art has attempted to deal with this problem in various ways. For example, U.S. Pat. Nos. 5,041,130 and 5,350,420 to Cosgrove et al. disclose a releasable interlock using a pin and J-shaped slot which is released and engaged with a partially rotary, partially axial movement of the handle, while Baxter International, Inc.'s Model 4450 uses an axially engageable (but non-releasable) interlock.

The present invention is directed to resolving one or all of the problems mentioned above.

SUMMARY OF THE INVENTION

The invention, in a first aspect, is an apparatus for holding a flexible annuloplasty ring during implantation. The apparatus comprises a top piece including a bottom surface sized to engage substantially all of the inner diameter of the annuloplasty ring and finished to grip the annuloplasty ring; a bottom piece including a top surface sized to engage substantially all of the inner diameter of the annuloplasty ring and finished to grip the annuloplasty ring; and a haft capable of engaging the top and bottom pieces to releasably clamp the annuloplasty ring therebetween.

In a second aspect, the invention is a method of manipulating a flexible annuloplasty ring for implantation. The method comprises disposing the annuloplasty ring between a top piece and a bottom piece; and engaging the top piece and the bottom piece with a haft to releasably clamp the annuloplasty ring between the top and bottom pieces.

In a third aspect, the invention comprises an annuloplasty ring and holder combination, adapted for allowing a surgeon to readily implant the annuloplasty ring in an annulus of a patient's heart. The apparatus comprises a top piece including a bottom surface sized to engage at least a portion of the inner diameter of the annuloplasty ring, and a bottom piece, coupled to said top piece, and including a top surface sized to engage at least a portion of the inner diameter of the annuloplasty ring. In preferred embodiments, one or more of the bottom surface and the top surface are finished to grip the annuloplasty ring. In alternative embodiments, the top and bottom surface engage the ring by compression only, with no finished surface. In another preferred embodiment, the combination comprises a haft to engage the top and bottom pieces and couple them together, thereby releasably clamping the annuloplasty ring therebetween.

BRIEF DESCRIPTION OF THE DRAWINGS

The invention may be understood by reference to the following description taken in conjunction with the accompanying drawings, in which like reference numerals identify like elements, and in which.

Figure 1:
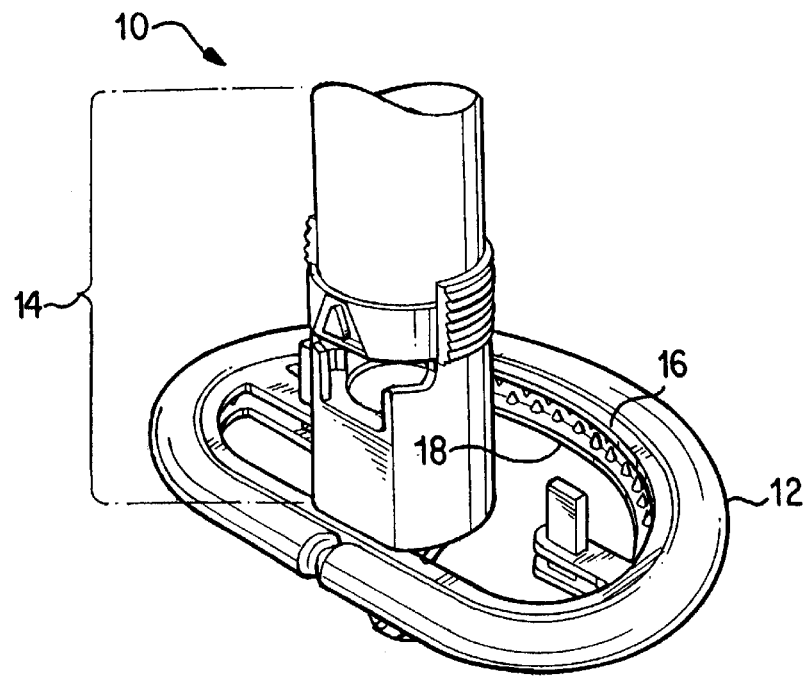
FIG. 1 is an isometric, top view of an embodiment of an apparatus for implanting a flexible annuloplasty ring in accordance with the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Figure 2:
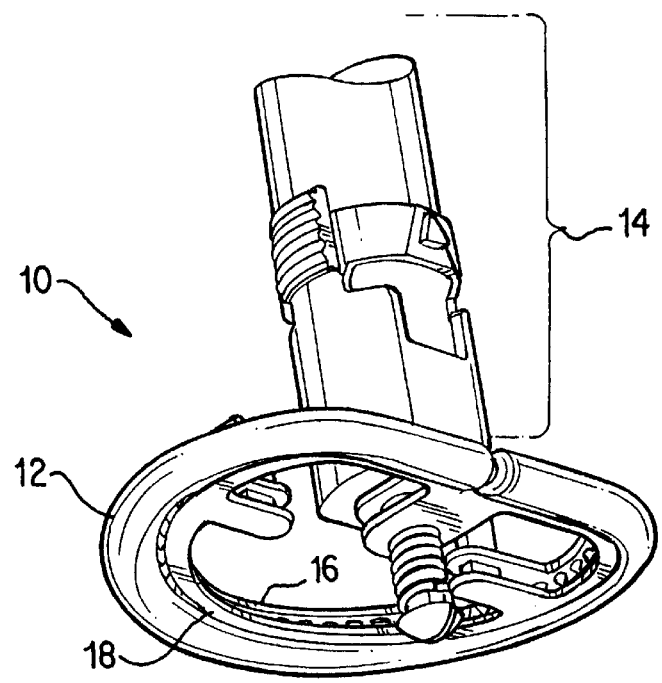
FIG. 2 is an isometric, bottom view of the embodiment in FIG. 1.
Figure 3:
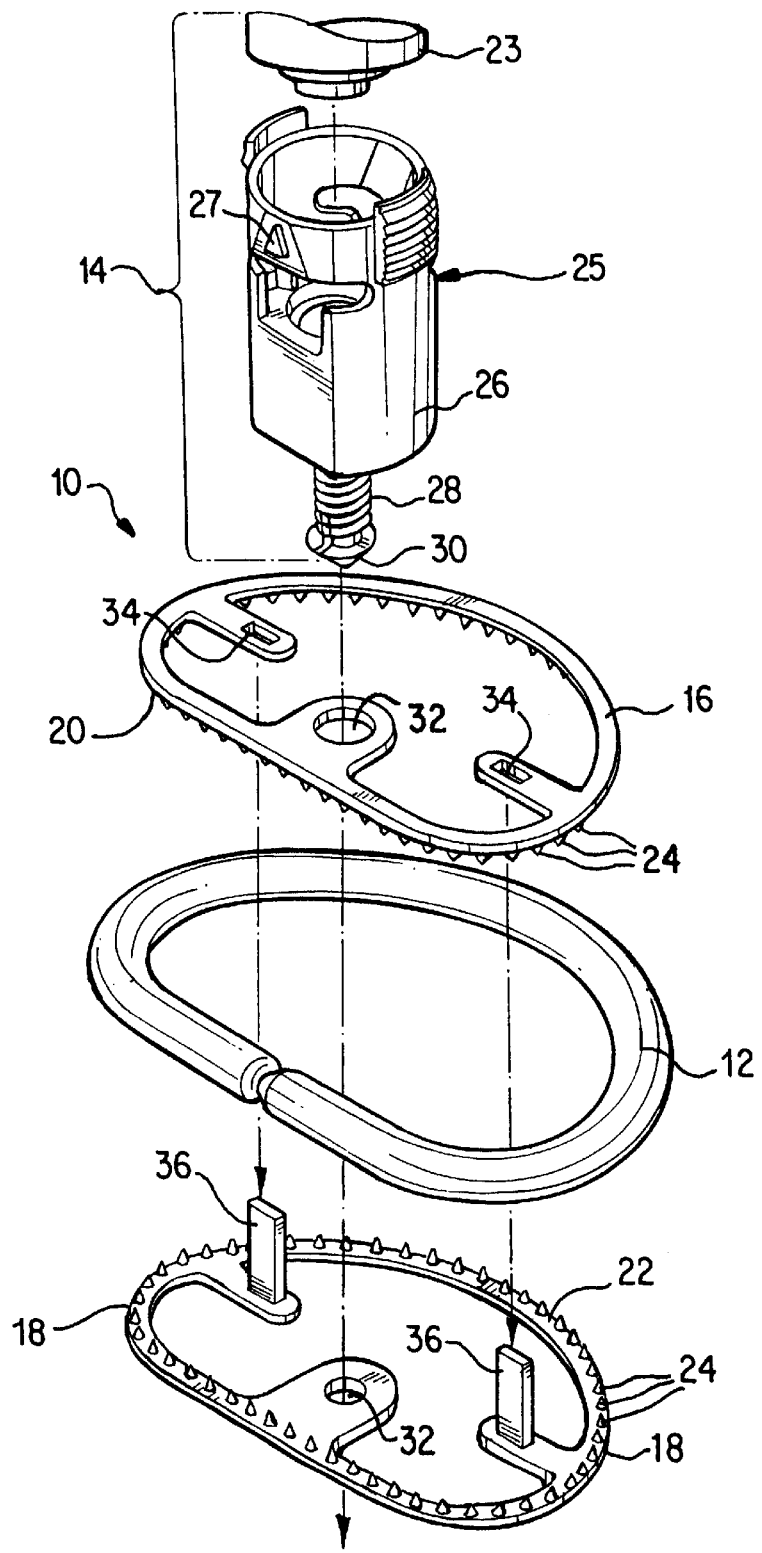
FIG. 3 is a partially exploded, isometric, top view of the embodiment of FIGS. 1–2.
Figure 4:
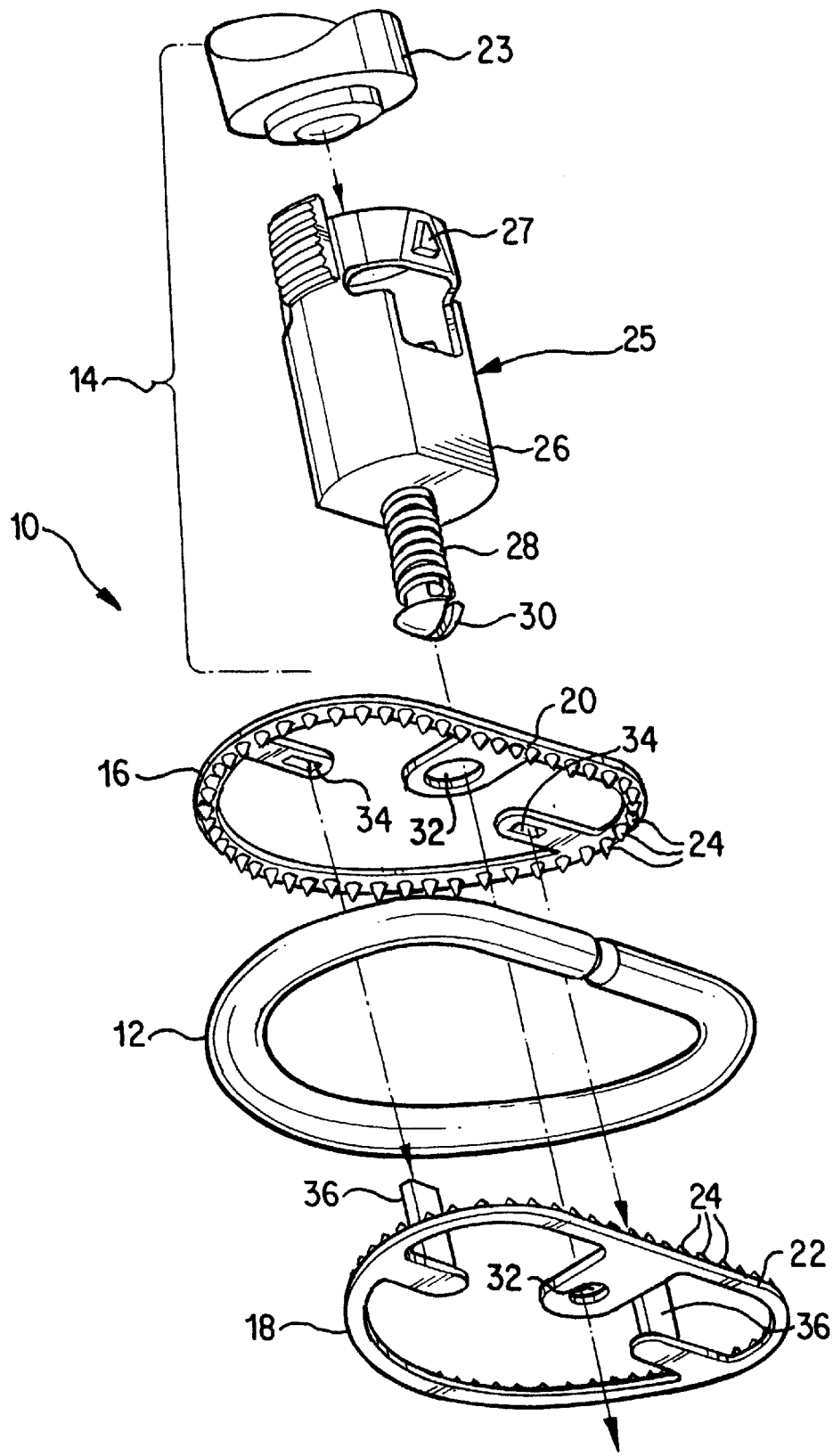
FIG. 4 is a partially exploded, isometric, bottom view of the embodiments of FIGS. 1–3.

Turning now to the drawings, FIGS. 1–4 illustrate an apparatus 10 for implanting an annuloplasty ring 12 in accordance with the present invention. More particularly, each of FIGS. 1–4 presents an isometric view of the apparatus 10, FIGS. 1 and 3 from the top and FIGS. 2 and 4 from the bottom. FIGS. 3–4 are exploded. For present purposes, "top" and "bottom" are defined relative to whether the subject is proximal or distal to the point at which the surgeon will manipulate the apparatus 10 and annuloplasty ring 12, i.e., the haft 14. Thus, the haft 14 in the embodiment illustrated extends from the "top" of the apparatus 10, as shown best in FIG. 1.

The annuloplasty ring 12 in the illustrated embodiment is a flexible annuloplasty ring, shown best in FIGS. 3–4, such as is known in the art. As used herein, the term "flexible" means non-rigid, or possessing some significant degree of pliancy. Those skilled in the art having the benefit of this disclosure will appreciate that annuloplasty rings are typically classified as either "rigid" or "flexible," with flexible annuloplasty rings having a varying degrees of pliancy. Some annuloplasty rings exhibit characteristics of both rigid and flexible annuloplasty rings. These rings are sometimes referred to as "semi-rigid." For purposes of this disclosure, semi-rigid annuloplasty rings are considered flexible annuloplasty rings. The annuloplasty ring 12 may be any such flexible annuloplasty ring.

The annuloplasty ring 12 illustrated also is an "incomplete" ring. As those skilled in the art will further appreciate, annuloplasty rings may also be classed as "complete" or "incomplete," depending on whether the circumference of the ring is continuous or broken. Although the annuloplasty ring 12 of the illustrated embodiment is incomplete, this characteristic is not material to the practice of the invention. Thus, the annuloplasty ring 12 may be any flexible annuloplasty ring, whether complete or incomplete, known to the art.

The apparatus 10 comprises, in addition to the haft 14 mentioned above, a first piece 16 and a second piece 18. The first piece 16, being more proximal to the haft 14, shall hereafter be referred to as the "top" piece 16. The second piece 18, being more distal to the haft 14, shall hereafter be referred to as the "bottom" piece 18. The haft 14 is capable of engaging the top piece 16 to the bottom piece 18, as is shown in FIGS. 1–2, to releasably clamp the annuloplasty ring 12 therebetween, in a manner discussed more fully below.

In one embodiment, as shown in FIGS. 3 and 4, the top piece 16 has a bottom surface 20 and the bottom piece 18 has a top surface 22 sized to engage substantially all of the inner diameter of the annuloplasty ring 12 and are finished to grip the annuloplasty ring 12. "Substantially" all the inner diameter of the annuloplasty ring means enough to provide adequate support during implantation to facilitate implantation and inhibit deformation. Persons of skill in the art will appreciate that the amount of engagement of the inner diameter of the ring necessary to achieve the foregoing goals will be dependent to a large degree on the flexibility of the annuloplasty ring 12. However, it will be readily appreciated that adequate support may be achieved by embodiments in which only a portion of the entire inner diameter may be engaged (i.e., less than the entire inner diameter). In the embodiment illustrated, the bottom surface 20 and the top surface 22 each engages the entire inner diameter of the annuloplasty ring 12.

The bottom surface 20 and the top surface 22 need not mirror one another in all embodiments. That aspect of the illustrated embodiment results from the symmetrical design of the annuloplasty ring 12 in the particular embodiment. Note also that the top piece 16 and the bottom piece 18 do not necessarily require continuous or identical cross-sections in all embodiments as do those in the illustrated embodiment. Similarly, the engagement of the inner diameter of the annuloplasty ring may be continuous or interrupted. The bottom surface 20 and the top surface 22 are also finished to grip the annuloplasty ring 12. In the illustrated embodiment, the surfaces 20, 22 are finished with a plurality of teeth 24. Other types of finishes may also be acceptable in alternative embodiments. For instance, in various alternative embodiments, the surfaces 20, 22 may be spiked, grooved, gnurled, or roughened, or some permutation of the above. Where the surfaces 20, 22 are roughened, this may accomplished by deposition of a grit during fabrication. The surfaces 20, 22 need not necessarily be finished in the same manner although they are in the embodiment illustrated. The desired finish will depend in large degree on the material from which the annuloplasty ring 12 is fabricated, as will be appreciated by those skilled in the art having the benefit of this disclosure. For instance, softer materials will be more amenable to more drastic structures, such as teeth or spikes, than will harder materials. Conversely, harder materials will be more amenable to finer structures, such as grooves.

Figure 5:
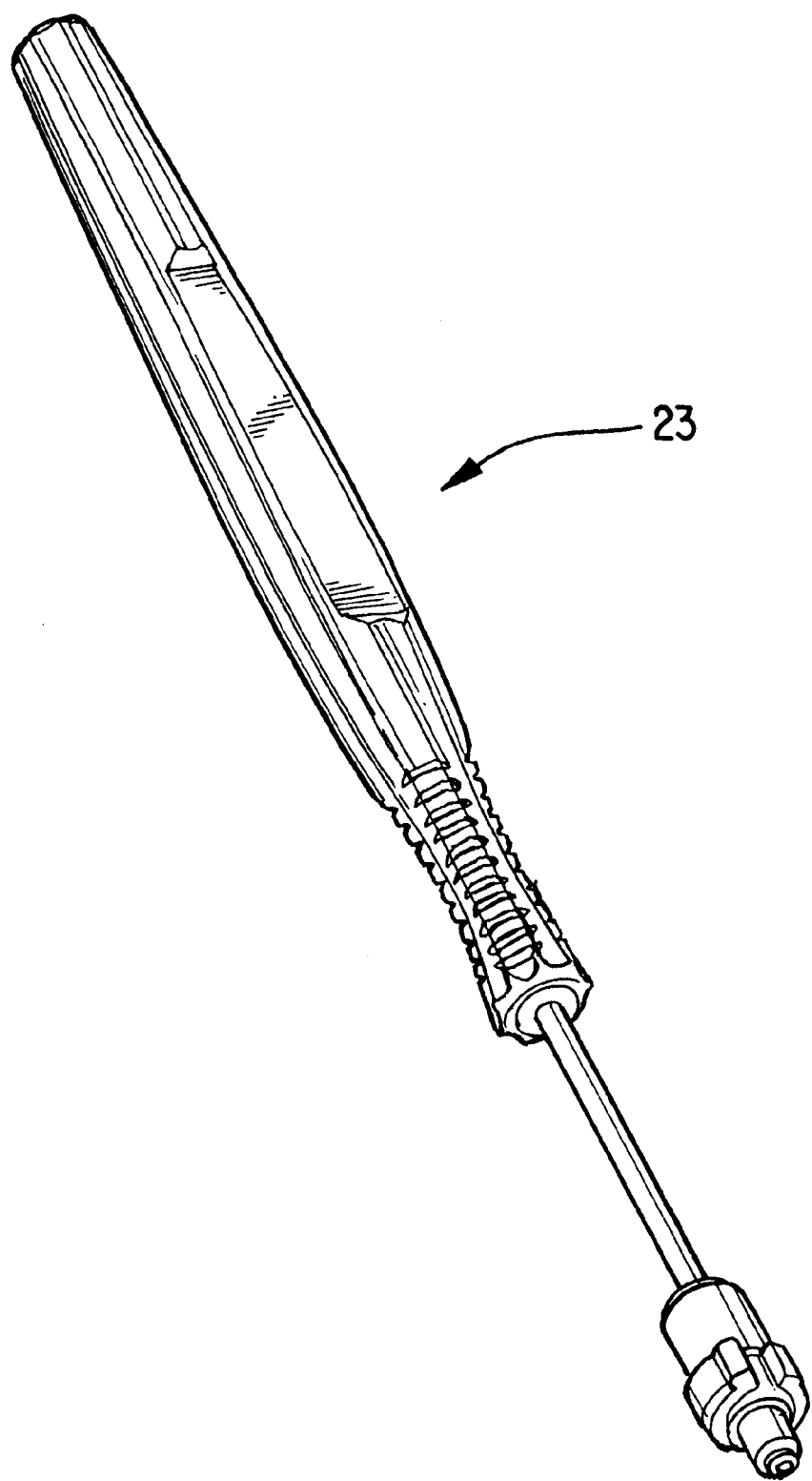
FIG. 5 is an isometric view of the handle that comprises a part of the haft.

The haft 14 includes, in the embodiment illustrated, a VH200 handle 23, shown in FIG. 5, commercially available from Sulzer Carbomedics Inc., Austin, Tex., the assignee of this invention. However, the invention is not so limited. Other commercially available handles suitable for this purpose may become apparent to those skilled in the art having the benefit of this disclosure. Any such handle may be used to implement the present invention.

The haft 14, in this particular embodiment, includes an adapter 25 intermediate the handle 23 and the top piece 16. The adapter 25 includes a button 27 to assist in orienting the handle 23 and intermediate piece 25. The adapter 25 terminates in a screw 28 at its distal, or bottom, end 26. The screw 28, in turn, terminates in a boss 30 that helps prevent the haft 14 from disengaging from the top piece 16 and the bottom piece 18 during or after implantation. More particularly, the screw 28 is used during assembly to engage the top and bottom pieces 16, 18 and to thereby clamp the annuloplasty ring 12 therebetween in a manner described further below.

As is apparent from the above discussion, the invention admits a wide degree of variation in structure within the scope and spirit of the invention. For example, the top and bottom pieces 16, 18 comprise, by way of example and illustration, but one means for releasably clamping the annuloplasty ring 12 to engage substantially all of the inner diameter thereof and to grip the annuloplasty ring 12 during implantation. In an alternative embodiment, the top and bottom pieces may engage only a portion or portions of the inner diameter of the annuloplasty ring. More particularly, the top and bottom pieces may comprise gripping protrusions extending radially from therefrom, which cooperate to clampingly engage the inner diameter of the ring. Similarly, the haft 14 in the embodiment illustrated comprises, also by way of example and illustration, but one means for manipulating the apparatus 10 to handle the annuloplasty ring 12 during implantation. Other, equivalent, structures performing these identical functions as may become apparent to those skilled in the art having the benefit of this disclosure and may be employed in alternative embodiments.

The apparatus 10 may be constructed of any suitable biocompatible material, e.g., material compatible with blood and/or tissue. The present invention is not limited by the material used to construct the apparatus 10. Biocompatible materials should be used because the apparatus 10 may contact the patient's tissue for, perhaps, an hour or more during implantation. Suitable biocompatible materials will be sufficiently rigid to support the annuloplasty ring 12 during implantation.

The apparatus 10 may be formed or pre-formed, for example, from any sufficiently rigid metal or synthetic polymer, or may be a composite of materials. Suitable metals include a cobalt-chromium-nickel-molybdenum-iron alloy (ASTM F1058) marketed under the name Elgiloy(by Elgiloy Company, Elgin, Ill., and other stainless steels or alloys having similar properties, such as cobalt, titanium, and alloys thereof, might be used. Suitable synthetic polymers include, but are not limited to thermoplastics, such as polyolefins, polyesters, polyamides, polysulfones, acrylics, polyacrylonitriles, and polyaramides, such as to polyetheretherketone (PEEK).

The manner in which the apparatus 10 may be fabricated will depend, in large degree, upon the materials from which the various pieces are manufactured. Suitable fabrication techniques may include extrusion, stamping, and molding, depending on the materials employed. The selection of materials and the suitable fabrication techniques applicable thereto will be apparent to those skilled in the art having the benefit of this disclosure.

Referring now to FIGS. 3–4, the apparatus 10 may be assembled by disposing the annuloplasty ring 12 between the top piece 16 and the bottom piece 18. The slots 34 on the top piece 16 are then aligned with the posts 36 on the bottom piece 18 and the top piece and the bottom piece are pressed together. The boss 30 then snaps through the co-aligned apertures 32 in the top and bottom pieces 16, 18 and will not snap out of those apertures 32 without an inordinate amount of force. Once the boss 30 is snapped in, the haft 14 may be rotated clockwise until the screw 28 fully engages both the top and bottom pieces 16, 18 to clamp the annuloplasty ring 12 therebetween. The assembled apparatus 10 is illustrated in FIGS. 1–2.

The apparatus 10 is then ready for use in implanting the flexible annuloplasty ring 12. The surgeon may use the haft 14 to manipulate the apparatus 10 and position the annuloplasty ring 12 for implantation in accordance with otherwise conventional techniques. Once the annuloplasty ring 12 is implanted, the haft 14 is rotated counterclockwise to disengage the top and bottom pieces 16, 18 and unclamp the annuloplasty ring 12. In the embodiment illustrated, the boss 30 is intended to prevent the haft 14 from disengaging the top and bottom pieces 16, 18. The apparatus 10 may be disengaged by "buttonholing" it out of the annuloplasty ring 12, i.e., the annuloplasty ring 12 is gradually stretched radially and repositioned distally from the haft 14 beyond the distal end of the bottom piece 18.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An annuloplasty ring and holder combination comprising:
   an annuloplasty ring having an inner diameter; and
   a holder comprising a clamp, said clamp engaging said annuloplasty ring and comprising:
   a top piece comprising a bottom surface engaging the inner diameter of said ring;
   a bottom piece comprising a top surface engaging the inner diameter of said ring;
   wherein said top piece and said bottom piece are coupled together by a haft and wherein at least a portion of said inner diameter of said ring is releasably clamped between said top piece and said bottom piece.

2. The annuloplasty ring and holder combination of claim 1, wherein said top piece engages a portion of the inner diameter of the ring.

3. The annuloplasty ring and holder combination of claim 1, wherein said top piece engages substantially all of the inner diameter of the ring.

4. The annuloplasty ring and holder combination of claim 3, wherein said top piece engages the entire inner diameter of the ring.

5. The annuloplasty ring and holder combination of claim 1, wherein said bottom piece engages a portion of the inner diameter of the ring.

6. The annuloplasty ring and holder combination of claim 1, wherein said bottom piece engages substantially all of the inner diameter of the ring.

7. The annuloplasty ring and holder combination of claim 6, wherein said bottom piece engages the entire inner diameter of the ring.

8. The annuloplasty ring and holder combination of claim 1, said bottom piece comprising a post and said top piece comprising a slot, and wherein said post engages said slot when said top piece and said bottom piece are coupled together.

9. The annuloplasty ring and holder combination of claim 1, wherein said bottom surface comprises a finish for gripping said ring.

10. The annuloplasty ring and holder combination of claim 1, wherein said top surface comprises a finish for gripping said ring.

* * * * *